(12) United States Patent
Bharat et al.

(10) Patent No.: US 10,786,310 B2
(45) Date of Patent: Sep. 29, 2020

(54) QUALITY ASSURANCE AND DATA COORDINATION FOR ELECTROMAGNETIC TRACKING SYSTEMS

(71) Applicant: KONINKLIJKE PHILIPS N.V., Eindhoven (NL)

(72) Inventors: Shyam Bharat, Arlington, MA (US); Ehsan Dehghan Marvast, New York, NY (US); Cynthia Ming-Fu Kung, New York, NY (US); Amir Mohammad Tahmasebi Maraghoosh, Melrose, MA (US); Sandeep M. Dalal, Cortlandt Manor, NY (US); Jochen Kruecker, Washington, DC (US); Antonio Bonillas Vaca, Best (NL); Douglas Allen Stanton, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 807 days.

(21) Appl. No.: 15/124,078

(22) PCT Filed: Mar. 17, 2015

(86) PCT No.: PCT/IB2015/051924
§ 371 (c)(1),
(2) Date: Sep. 7, 2016

(87) PCT Pub. No.: WO2015/145300
PCT Pub. Date: Oct. 1, 2015

(65) Prior Publication Data
US 2017/0014192 A1 Jan. 19, 2017

Related U.S. Application Data

(60) Provisional application No. 61/969,285, filed on Mar. 24, 2014.

(51) Int. Cl.
*A61B 34/20* (2016.01)
*A61N 5/10* (2006.01)
(Continued)

(52) U.S. Cl.
CPC .............. *A61B 34/20* (2016.02); *A61B 5/062* (2013.01); *A61B 17/3403* (2013.01);
(Continued)

(58) Field of Classification Search
CPC ..... A61B 34/20; A61B 5/062; A61B 17/3403; A61B 2034/2051; A61B 2017/00274;
(Continued)

(56) References Cited

U.S. PATENT DOCUMENTS 5,494,039 A 2/1996 Onik et al.
7,085,400 B1 8/2006 Holsing et al.
(Continued)

*Primary Examiner* — Theodore J Stigell
*Assistant Examiner* — Sean A Frith

(57) ABSTRACT

An electromagnetic ("EM") tracking configuration system employs an EM quality assurance ("EMQA") (30) and EM data coordination ("DC") system (70). For the EMQA system (30), an EM sensor block (40) includes EM sensor(s) (22) positioned and oriented to represent a simulated electromagnetic tracking of interventional tool(s) inserted through electromagnetic sensor block (40) into an anatomical region. As an EM field generator (20) generates an EM field (21) encircling EM sensor(s) (22), an EMQA workstation (50) tests an EM tracking accuracy of an insertion of the interventional tool(s) through the EM sensor block (40) into the anatomical region. For the EMDC system (70), as EM field generator (20) generates EM field (21) encircling a mechanical interaction of EM calibration tool(s) (80) with a grid (120) for guiding interventional tool(s) through gird (120) into an anatomical region, the electromagnetic data coordination workstation (90) establishes a coordination system for electromagnetically tracking an insertion of the interventional tool(s) through grid (120) into the anatomical region.

15 Claims, 7 Drawing Sheets

(51) Int. Cl.
*A61B 17/34* (2006.01)
*A61B 5/06* (2006.01)
*A61B 17/00* (2006.01)

(52) U.S. Cl.
CPC ......... *A61N 5/1027* (2013.01); *A61N 5/1075* (2013.01); *A61B 2017/00274* (2013.01); *A61B 2017/00725* (2013.01); *A61B 2017/3411* (2013.01); *A61B 2034/2051* (2016.02); *A61B 2560/0223* (2013.01); *A61N 5/1001* (2013.01); *A61N 2005/1012* (2013.01)

(58) Field of Classification Search
CPC .. A61B 2017/00725; A61B 2017/3411; A61B 2560/0223; A61N 5/1027; A61N 5/1075; A61N 5/1001; A61N 2005/1012
See application file for complete search history.

(56) References Cited

U.S. PATENT DOCUMENTS

| | | |
|---|---|---|
| 7,879,045 B2 | 2/2011 | Gielen et al. |
| 9,733,336 B2 | 8/2017 | Shen et al. |
| 10,143,852 B2 | 12/2018 | Bharat et al. |
| 2003/0065260 A1* | 4/2003 | Cheng .................. A61B 8/0833 600/427 |
| 2003/0233123 A1* | 12/2003 | Kindlein .............. A61N 5/1031 607/2 |
| 2007/0043291 A1* | 2/2007 | Fidel ........................ A61B 8/12 600/439 |
| 2007/0232882 A1* | 10/2007 | Glossop ............... A61B 8/0841 600/407 |
| 2008/0216239 A1* | 9/2008 | Luginbuhl ........... A61B 5/0555 5/601 |
| 2010/0016710 A1* | 1/2010 | Kumar .................. A61B 5/055 600/425 |
| 2010/0249595 A1 | 9/2010 | Xu et al. |
| 2012/0253100 A1* | 10/2012 | Chisholm .......... A61B 17/3403 600/8 |
| 2013/0116548 A1* | 5/2013 | Kumar ................ A61B 8/0841 600/424 |
| 2013/0144832 A1 | 6/2013 | Li |
| 2013/0303895 A1 | 11/2013 | Littrup et al. |
| 2013/0310680 A1* | 11/2013 | Werahera ............ A61B 1/0016 600/411 |
| 2014/0350325 A1* | 11/2014 | Van Appeldoorn .......................... A61N 5/1007 600/8 |
| 2014/0357977 A1* | 12/2014 | Zhou ..................... A61B 5/061 600/409 |
| 2015/0051861 A1 | 2/2015 | Kruecker et al. |

* cited by examiner

QUALITY ASSURANCE AND DATA COORDINATION FOR ELECTROMAGNETIC TRACKING SYSTEMS

CROSS-REFERENCE TO PRIOR APPLICATIONS

This application is the U.S. National Phase application under 35 U.S.C. § 371 of International Application Serial No. PCT/IB2015/051924, filed on Mar. 17, 2015, which claims the benefit of U.S. Application Ser. No. 61/969,285, filed on Mar. 24, 2014. These applications are hereby incorporated by reference herein.

The present invention generally relates to an electromagnetic ("EM") tracking system incorporated within an interventional procedure (e.g., a prostate brachytherapy procedure). The present invention specifically relates to a quality assurance for validating and improving a performance accuracy of the EM tracking system and to an establishment of a patent coordinate system for EM tracking of interventional tools (e.g., ultrasound probes, catheters, needles, etc.).

As shown in FIG. 1, in an exemplary prostate brachytherapy procedure 10 with EM tracking functionality as known in the art, an EM field 21 is generated by an EM field generator 20 that is located close to a pelvic region of a patient 11. For a conventional planar EM field generator 20 (e.g., a brick-shaped EM field generator), a tracking field of view ("FOV") may be 50×50×50 cm. A typical position for EM field generator 20 during the prostate brachytherapy 10 would be above an abdomen of patient 11, because this position typically leads to minimal physical interference with the existing clinical setup. EM field generator 20 is usually held in place using a mounting arm (not shown) that is attached to a treatment table (not shown). EM field generator 20 may be parallel to the table or angled towards the prostate, depending on the patient-specific geometry and set-up.

More importantly during prostate brachytherapy 10, the position of EM field generator 20 with respect to the tracked pelvic region of patient 11 plays a vital role in an achievable tracking accuracy of an intervention of a catheter/needle 13 with a prostate 15 of patient 11 as guided by a grid template 12 and an achievable tracking accuracy of an imaging of prostate 15 by an ultrasound probe 14 as guided by grid template 12. In other words, the accuracy of the EM measurements from each EM sensor (not shown) coupled to catheter/needle 13 and to ultrasound probe 14 depends on a position of each EM sensor relative to EM field generator 20. This is due to the fact that EM field 21 produced by EM field generator 20 is not perfectly homogeneous. More particularly, there may be sections of EM field 21 where the tracking accuracy may be compromised in terms of increased absolute position errors and/or noise in the measurements. Therefore, prior to EM-tracked prostate brachytherapy procedure 10, it is necessary to validate the accuracy of the EM system in the clinical environment.

Furthermore, a treatment plan based on the transrectal ultrasound ("TRUS") images from ultrasound probe 14 may indicate a distance through holes of grid 12 of each catheter/needle 13 to achieve an intended dose delivery for prostate 15. In such a fusion brachytherapy system of EM field generator 20 and ultrasound probe 14, grid 12 also serves to determine a common data coordinate system for EM data and TRUS data. To establish this coordinate system in EM space prior to prostate brachytherapy procedure 10, an EM-tracked tool (not shown) is positioned at different holes of grid 12 and the recorded EM data is fit to the known grid hole pattern.

More particularly, to achieve an accurate definition of the coordinate system, the EM-tracked tool must be positioned perfectly perpendicular to each grid hole and at the same depth. Otherwise, if the EM-tracked tool is not perpendicular to the grid hole and/or is inserted to varying depths in different holes, the resulting estimated grid plane will not be accurately representative of the actual grid 12. This will result in errors in the estimated location of catheter/needle 13 with respect to grid 12 as compared to the actual location of catheter/needle 13 with respect to grid 12. It will also result in a distorted/inaccurate three-dimensional ("3D") image reconstruction of the anatomy in the grid coordinate system (i.e., patient coordinate system). Therefore, prior to EM-tracked prostate brachytherapy procedure 10, it is also necessary to facilitate an accurate and repeatable definition of the grid plane to thereby ensure high EM tracking accuracy during procedure 10.

The present invention proposes to provide a system for quality assurance in validating and improving a performance accuracy of the EM tracking system and an easy-to-use system for establishing a patent coordinate system for EM tracking of interventional tools (e.g., ultrasound probes, catheters, needles, etc.).

One form of the present invention is an EM quality assurance ("EMQA") system employing an EM field generator, an EM sensor block, and an EMQA workstation. The EM sensor block includes one or more EM sensors positioned and oriented to represent a simulated electromagnetic tracking of one or more interventional tools inserted through the electromagnetic sensor block (40) into an anatomical region. As the EM field generator generates an EM field encircling the EM sensor(s), the EMQA workstation tests an electromagnetic tracking accuracy of an insertion of the interventional tool(s) through the electromagnetic sensor block into the anatomical region.

A second form of the present invention is an EM data coordination ("DC") system employing an EM field generator, one or more EM calibration tools, and a EMDC workstation. Each EM calibration tool has one or more EM sensors. As the EM field generator generates an EM field encircling the EM calibration tool(s) mechanically interacting with a grid for guiding one or more interventional tools into an anatomical region, the EMDC workstation establishes a coordination system for electromagnetically tracking an insertion of the interventional tool(s) through the grid into the anatomical region.

A third form of the present invention is an EM tracking configuration system employing both the aforementioned EMQA system and EMDC system on the same or different platforms.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
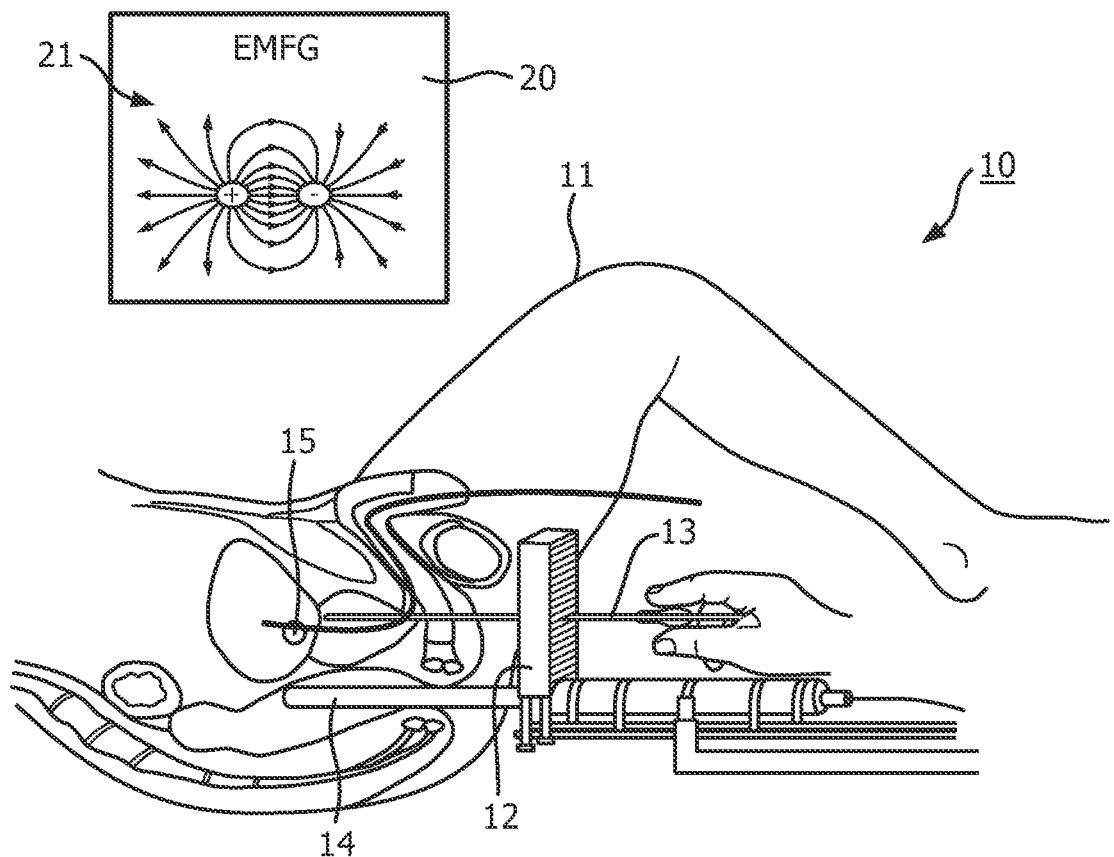
FIG. 1 illustrates an exemplary prostate brachytherapy procedure as known in the art.

To facilitate an understanding of the present invention, an exemplary embodiment of an EM tracking configuration system of the present invention as shown in FIG. 1 will be provided herein. From the description of the exemplary embodiment of the EM tracking configuration system, those having ordinary skill in the art will appreciate how to apply the operating principles of the present invention to (1) an implementation of the EM tracking configuration system as a stand-alone system for quality assurance and data coordination of EM tracking of interventional tools and (2) an incorporation of the EM tracking configuration system into various types of standard and innovative planning/guidance/navigation EM tracking platforms as known in the art.

Referring to FIG. 1, the EM tracking configuration system of the present invention is employs an EM quality assurance ("EMQA") system 30 and an EM data coordination system ("EMDC") system 70, both utilizing EM field generator 20 of any type as known in the art and one or more EM sensors 22 of any type as known in the art. The EM tracking configuration system is utilized to qualitatively configure EM field generator 20 and EM sensors 22 in a tracking arrangement specific to a patient-equipment geometry of a particular interventional procedure.

To this end, for quality assurance in validating and improving a performance accuracy of EM field generator 20 in tracking EM sensors 22, EMQA system 30 employs (1) a EM sensor block 40 containing a known positional and orientational arrangement of EM sensors 22 with respect to each other, and (2) an EM quality assurance ("EMQA") workstation 50 executing one or more validation test(s) of EM sensors 22 as contained within EM sensor block 40 based on a positioning of EM field generator 20 relative to EM sensor block 40 analogous to a positioning of EM field generator 20 relative to EM sensors 22 as coupled to interventional tools (e.g., ultrasound probe, catheter, needle, etc.) during an interventional procedure. In practice, EM sensors 22 may be removably or permanently contained within channels of EM sensor block 40, and the validation test(s) executed by EMQA workstation 50 may incorporate an additional EM sensor 22 as a reference EM sensor attached to or spatially positioned from EM sensor block 40 within the FOV of EM field generator 20.

On a patient by patient basis, EMDC system 70 employs (1) one or more EM calibration tools 80 in a known working relationship with EM sensors 22, and (2) an EM data coordination ("EMDC") system 90 to establish a patient coordinate system for EM tracking of interventional tools (e.g., ultrasound probe, catheter, needle, etc.). In practice, EM calibration tools 80 may include one or more interventional tools to be utilized during the interventional procedure, and one or more pieces of equipment to be utilized during the interventional procedure for guiding the interventional tools may serve as the basis for establishing the patent coordinate system.

Also in practice, (1) EM sensor block 40 may serve as an EM calibration tool 80, and (2) EMQA workstation 50 and EMDC workstation 90 may be individual physical workstations or logic workstations installed within a single physical platform (e.g., an EM planning/guidance/navigation platform).

To facilitate an understanding of the present invention, exemplary embodiments of the present invention will be provided herein directed to EMQA system 30 as shown in FIGS. 3-6 and EMDC system as shown in FIGS. 7-12 in the context of a prostate brachytherapy procedure. From the description of the exemplary embodiments, those having ordinary skill in the art will appreciate how to apply the operating principles of the present invention to any type of interventional procedure.

Figure 2:
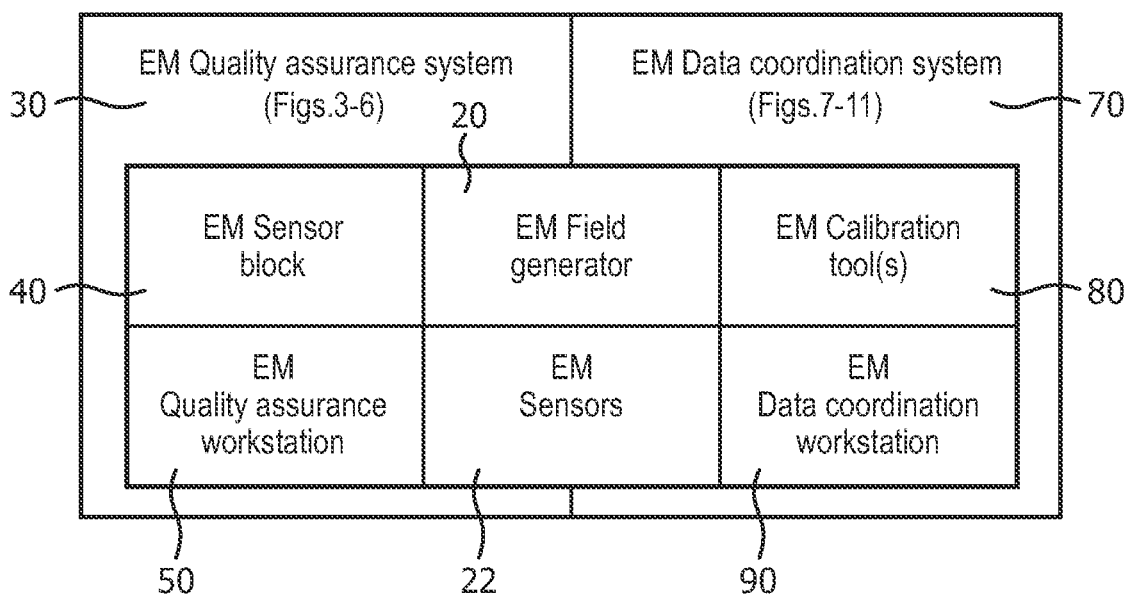
FIG. 2 illustrates an exemplary embodiment of a EM tracking configuration system in accordance with the present invention.
Figure 3:
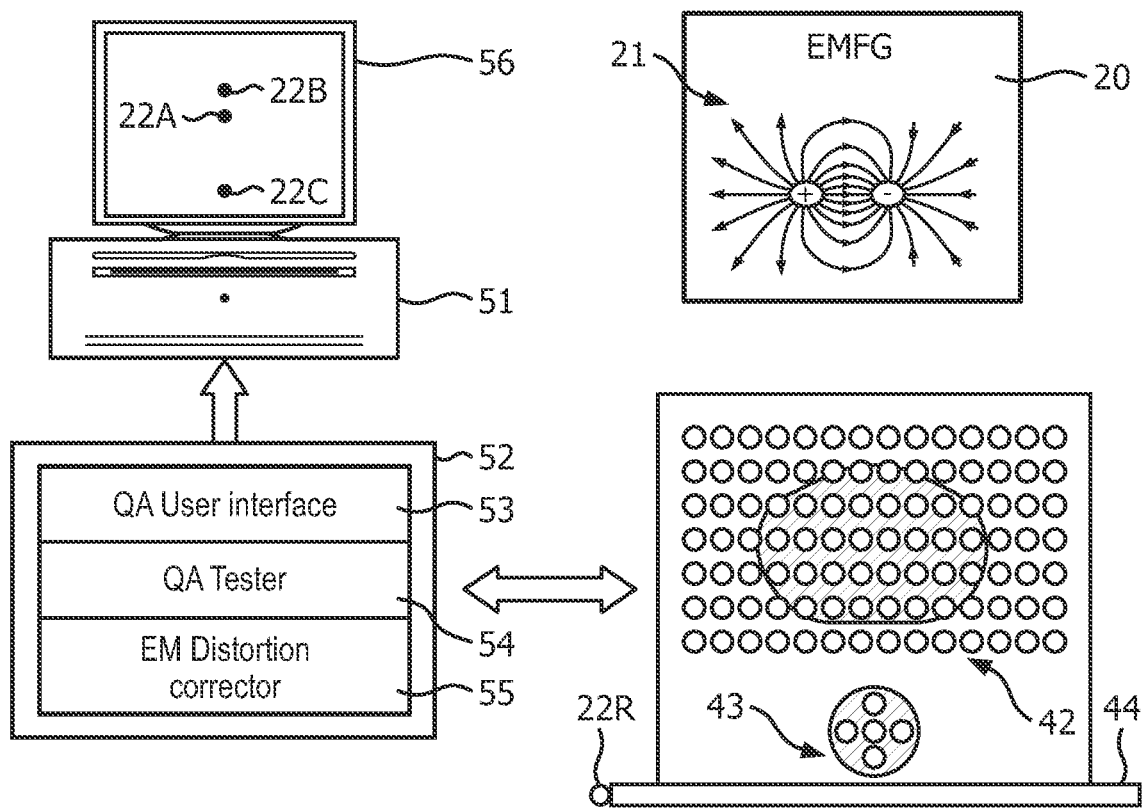
FIG. 3 illustrates an exemplary embodiment of an EM quality assurance system in accordance with the present invention.

Referring to FIG. 3, for the exemplary embodiment of EMQA system 30 (FIG. 2), a transparent, non-magnetic EM sensor block 41 contains a EM sensor group 42 and an EM sensor group 43. In a first embodiment, the EM sensors of groups 42 and 43 are EM coils permanently embedded in channels extending through EM sensor block 41. In a second embodiment, the EM sensors of groups 42 and 43 are EM coils removably inserted within the channels (e.g., via a guidewire).

As shown in FIG. 3, inter-sensor distances and sensor orientations of EM sensor groups 42 and 43 on EM sensor block 41 are chosen so as to represent a typical prostrate brachytherapy scenario. Specifically, an average height of a prostate and a rectum from a treatment table 44 is known apriori. Therefore, EM sensor grouping 42 is distanced relative to treatment table 44 whereby a subset of EM sensor group 42 represents channels covering a patient prostate area for guiding a catheter or a needle into the patient prostate area highlighted by a gray circle encircling the subset of EM sensor group 42. Similarly, EM sensor group 43 is distanced relative to treatment table 44 whereby EM sensor group 43 represents channels covering a patient rectum area for guiding a transrectal ultrasound ("TRUS") probe into the patient rectum area highlighted by a gray circle encircling EM sensor grouping 43. For example, as shown in a side view of EM sensor block 41 in FIG. 4, EM sensors 22A and 22B of EM sensor group 42 represent channels covering a patient prostate area 18 for guiding a catheter 16 into patient prostate area 18, and an EM sensor 22C of EM sensor group 43 represents channels covering a patient rectum area 19 for guiding a transrectal ultrasound ("TRUS") probe 17 into patient rectum area 19.

Figure 5:
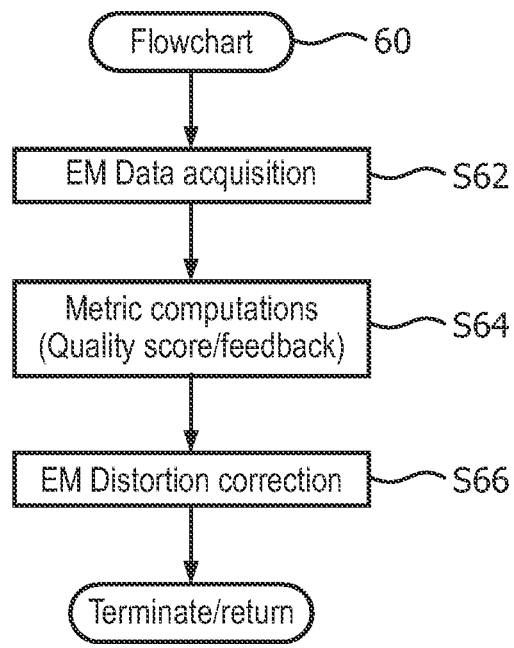
FIG. 5 illustrates a flowchart representative of an exemplary embodiment of an EM quality assurance method in accordance with present invention.
Figure 6:
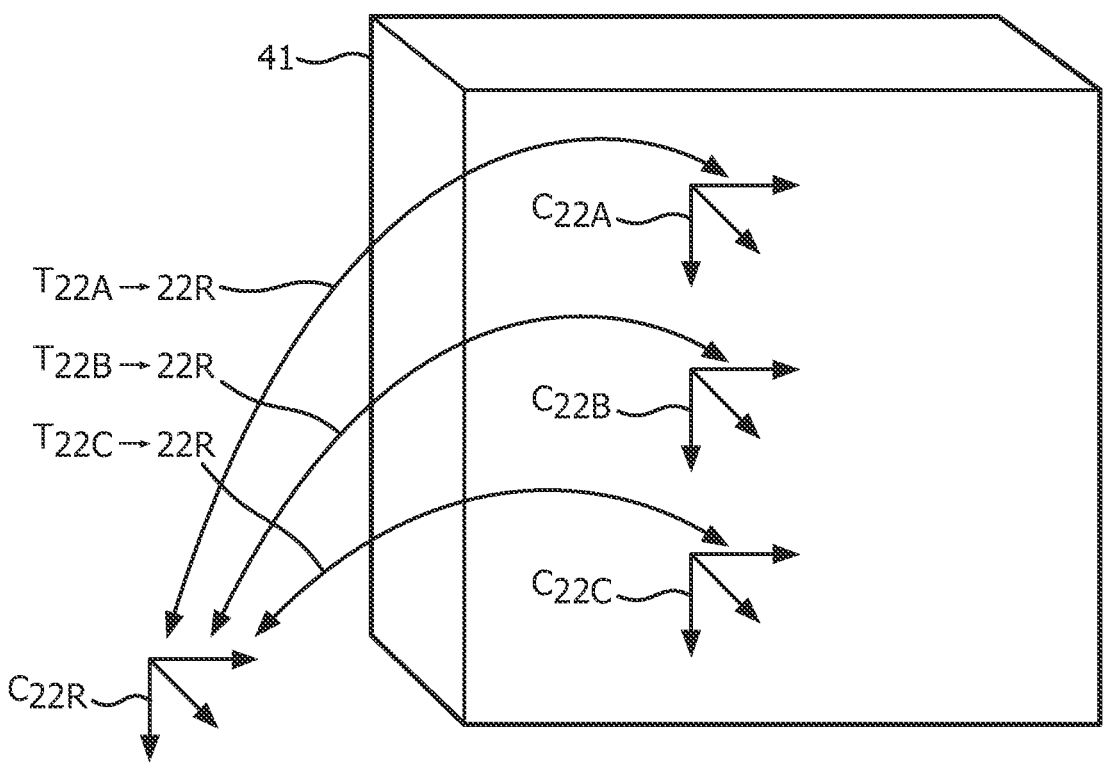
FIG. 6 illustrates an exemplary distortion correction in accordance with the present invention.

Referring back to FIG. 3, for the exemplary embodiment of EMQA system 30, an EMQA workstation 51 employs a network 52 of modules 53-55 and a EM reference sensor 22R for implementing a EM quality assurance method as represented by a flowchart 60 of FIG. 5. In practice, modules 53-55 are structurally configured as hardware, software, firmware and/or circuitry of workstation 51, and EM reference sensor 22R is of any type suitable to be coupled to treatment table 44 or any other fixed object within a FOV of EM field generator 20.

Figure 4:
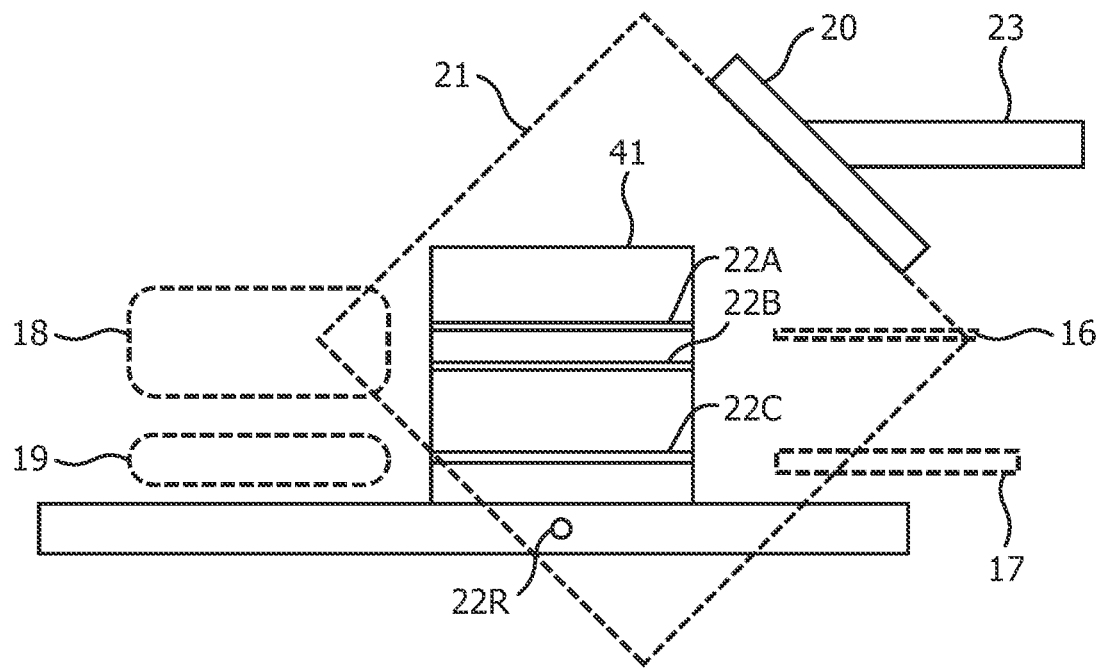
FIG. 4 illustrates an exemplary EM quality assurance set-up in accordance with the present invention.

Flowchart 60 will now be described herein in the context of FIG. 4, whereby EM field generator 20 is coupled to a mount 23 and angled toward EM sensor block 41, and EM sensors 22A-22C of EM sensor block 41 are utilized as tracking locations. Nonetheless, in practice, EM field generator 20 may have any orientation toward EM sensor block 41, and more or less EM sensors 22 may be utilized as tracking locations.

Referring to FIG. 5, a stage S62 of flowchart 60 encompasses an EM user interface 53 (FIG. 3), as directed by a user, acquiring EM data derived from EM field 21 of EM field generator 20 encircling EM sensors 22A-22C and 22R. In practice, if specific regions of EM field 21 afflicted with lower accuracy are known, EM user interface 53 may provide feedback to the user indicative of whether EM reference sensor 22R is in an "acceptable" position with respect to a position of EM field generator 20. If not, EM field generator 20 and/or EM reference sensor 22R may be repositioned to position EM reference sensor 22R in an "acceptable" position with respect to a position of EM field generator 20.

A stage S64 of flowchart 60 encompasses an EM tester 54 (FIG. 3) computing one or more metrics indicative of a quality of EM field generator 20 in tracking locations of EM sensors 22A-22C.

In a first metric embodiment (i), EM tester 54 computes a temporal measurement noise in a position estimate of EM sensors 22A-22C.

In a second metric embodiment (ii), EM tester 54 computes an EM-estimated inter-sensor distance of EM sensors 22A-22C and compares the computation to the known geometry of EM sensor block 41.

In a third metric embodiment (iii), EM tester 54 computes an absolute position of EM reference sensor 22R with respect to EM field generator 20.

In a fourth metric embodiment (iv), EM tester 54 computes two (2) or more of metric embodiments (i)-(iii) and assigns a cumulative "quality score" to the overall configuration of EM sensor block 41 and EM field generator 20.

Stage S64 further encompasses EM tester 54 (FIG. 3) providing any suitable type of user feedback representative of the computed quality of EM field generator 20 in tracking locations of EM sensors 22A-22C.

In a first feedback embodiment, a green light may be indicative of an acceptable configuration of EM sensor block 41 and EM field generator 20, and a red light may be indicative of an unacceptable configuration of EM sensor block 41 and EM field generator 20.

In a second feedback embodiment, as exemplary shown in FIG. 3, a two-dimensional ("2D") or a three-dimensional ("3D") accuracy map 56 for EM field generator 20 is generated and displayed to indicate the accuracy in tracking locations of EM sensors 22A-22C.

As applicable to any unacceptable inaccuracy in tracking locations of EM sensors 22A-22C, optional stage S66 of flowchart 60 encompasses an EM distortion corrector 55 (FIG. 6) estimating a function $f$ to correct any distortion within EM field 21. In one embodiment, as exemplarily shown in FIG. 6, a transformation ($T_{Emi}$, i∈{1,2,3}) from each of EM sensors 22A-22C ($C_{Emi}$, i∈{1,2,3}) to a reference coordinate system ($C_{Ref}$) associated with EM reference sensor 22R is known from a precise design of EM sensor block 41 in view of EM reference sensor 22R being contained within or registered to EM sensor block 41. Therefore, $T_{EMi \rightarrow Ref}$ are known transformations.

Furthermore, corresponding transformation matrices $T'_{EMi \rightarrow Ref}$ are measured by EM distortion corrector 55 in terms of measured relative position/pose of the EM sensors 22A-22C to the measured pose of EM reference sensor 22R whereby measured transformation matrices $T'_{EMi \rightarrow Ref}$ may be different from known transformation matrices $T_{EMi \rightarrow Ref}$ due to any inaccuracies of EM field generator 20 and distortions of EM field 20 inside EM sensor block 41. Therefore a correction function $f$ may be estimated by EM distortion corrector 55 in accordance with the following equation [1]:

$$T_{EMi \rightarrow Ref} = f(T'_{Emi \rightarrow Ref}) \qquad [1]$$

In practice, the above estimation of correction function $f$ is normally performed prior to the prostate brachytherapy procedure whereby during the procedure, various EM-EM transformations are utilized (e.g., EM needle→reference, EM TRUS→reference, etc.). For example, an EM measurement of a position of a TRUS probe may be corrected in accordance with the following equation [2]:

$$T_{P \rightarrow Ref} = f(T'_{P \rightarrow Ref}) \qquad [2]$$

where, $T'_{P \rightarrow Ref}$ is the measured probe to reference transformation matrix by the EM tracking system and $T_{P \rightarrow Ref}$ is the corrected probe to reference transformation matrix. This new probe position is more accurate and takes into account any distortion within EM field 21.

In practice, EM distortion corrector 55 may also include multiple locations for sensors 22A-22C and 22R. Therefore, for each such set 'x' of locations, a correction function '$f_x$' may be calculated. During the procedure, one of the functions '$f_x$' is used, depending on which EM transformation needs to be corrected. The appropriate function '$f_x$' is chosen based on sensor locations for the transformation to be corrected.

Referring back to FIGS. 3 and 4, the QA procedure is intended to be performed on EM sensor block 41 in a clinical environment just prior to the prostate brachytherapy procedure. Additionally, a positioning of EM reference sensor 22R on treatment table 44 may be re-verified prior to the procedure with the patient already on treatment table 44. This may represent the final QA check for EM system accuracy prior to the prostate brachytherapy procedure.

Figure 7:
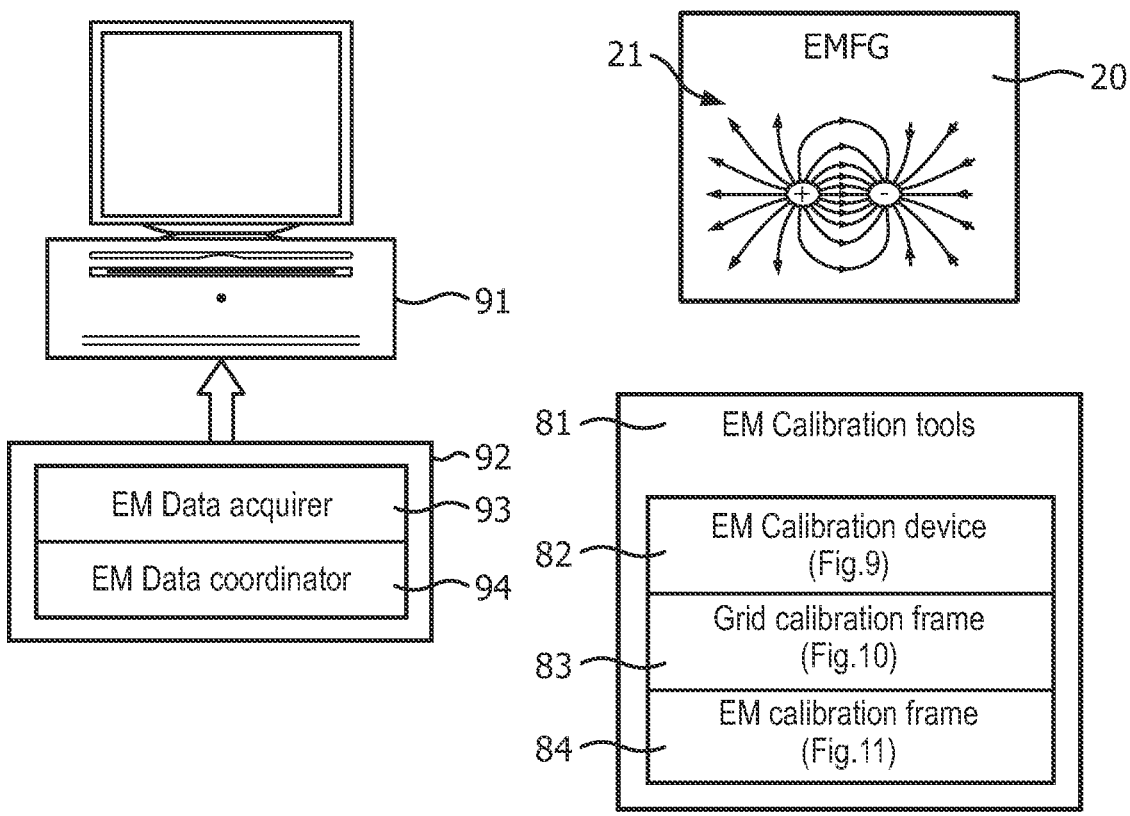
FIG. 7 illustrates an exemplary embodiment of an EM data coordination system in accordance with the present invention.
Figure 10:
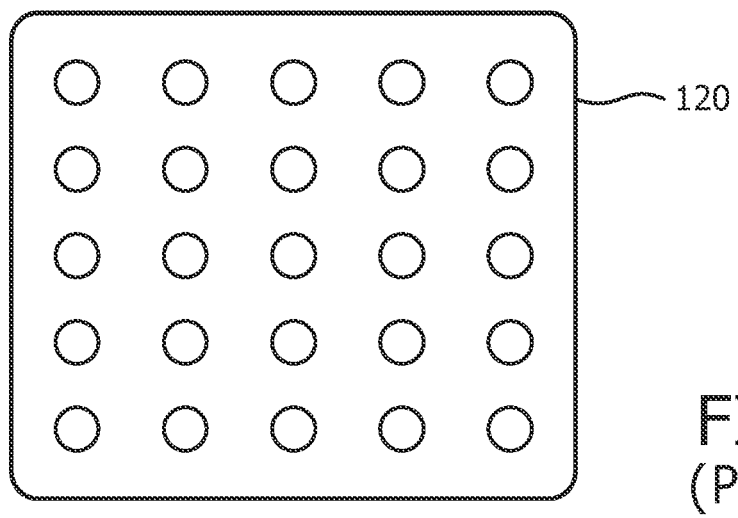
FIG. 10 illustrates a grid template as known in the art.

Referring to FIG. 7, for the exemplary embodiment of EMCD system 70 (FIG. 2), a set of EM calibration tools 81 employs (1) an EM calibration device 82 structurally configured to be controllable by hand or a robot, (2) a grid calibration frame 83 structurally configured to be attached to a prostate brachytherapy grid (aka template) as known in the art (e.g., grid 120 as shown in FIG. 10) and facilitate the use of EM calibration device 82, and (3) an EM calibration device 84 structurally configured to be mated with a prostate brachytherapy grid. EM calibration tools 81 are provided for facilitating a EMDC workstation 91 employing a network 92 of modules 93 and 94 for implementing a patient coordinate system establishment method as represented by a flowchart 100 of FIG. 8. In practice, modules 93 and 94 are structurally configured as hardware, software, firmware and/or circuitry of workstation 91.

Figure 8:
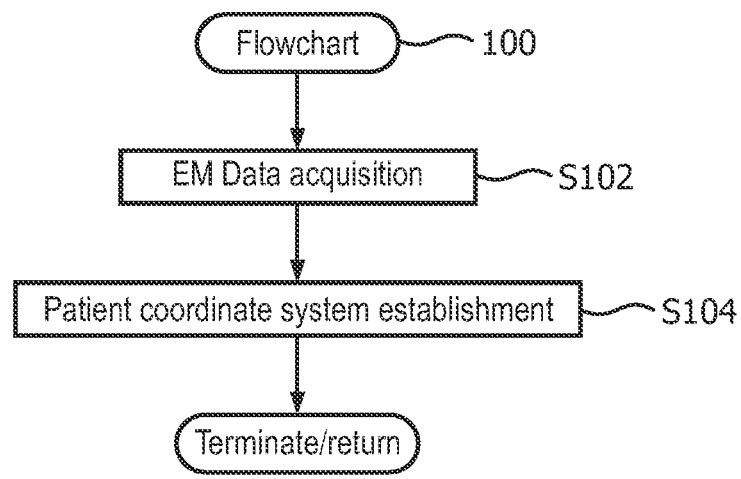
FIG. 8 illustrates a flowchart representative of an exemplary embodiment of an EM data coordination method in accordance with present invention.

Generally, referring to FIGS. 7 and 8, a stage S102 of flowchart 100 encompasses an EM data acquirer 93 acquiring EM data via manual or robotic control of one or more of EM calibration tools 81, and a stage S104 of flowchart 100 encompasses an EM data coordinator 94 establishing a patient coordinate system from the EM data. In practice, EM data coordinator 94 may implement a standard practice or an adaptive version thereof in establishing the coordinate system from the EM data. For example, a standard version of the present invention involves a definition of a grid plane in EM space by fitting the acquired EM data points to a "ground truth grid", which is obtained from a known inter-hole distances for the grid. Additionally, in an adaptive version, during the fitting process, a greater weight may be assigned to the specific grid holes utilized for needle/catheter/probe insertion to thereby ensure highest accuracy for such grid holes. The following is a description of exemplary embodiments of each EM calibration tool 81 in the context of the exemplary adaptive version of stage S104.

Figure 9A:
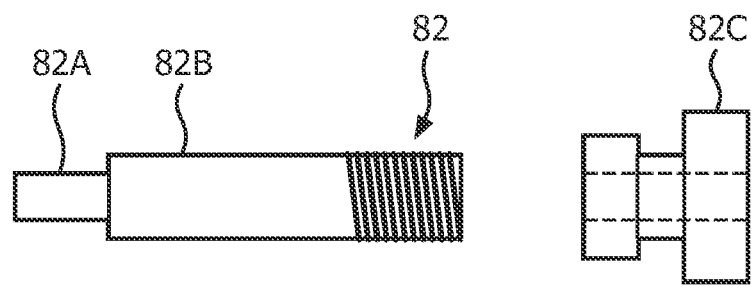
FIGS. 9A-9C illustrate an exemplary embodiment of an EM calibration device in accordance with the present invention.
Figure 9B:
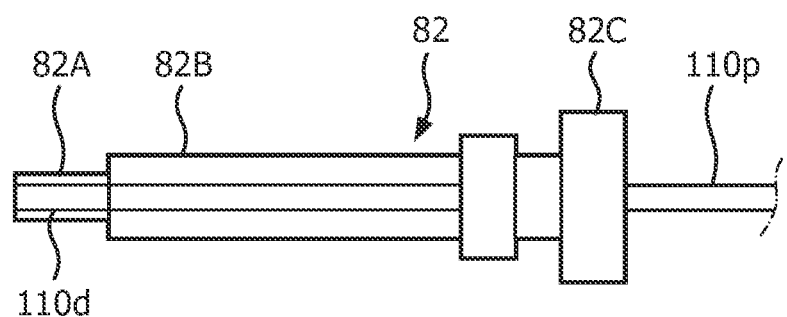
Figure 9C:
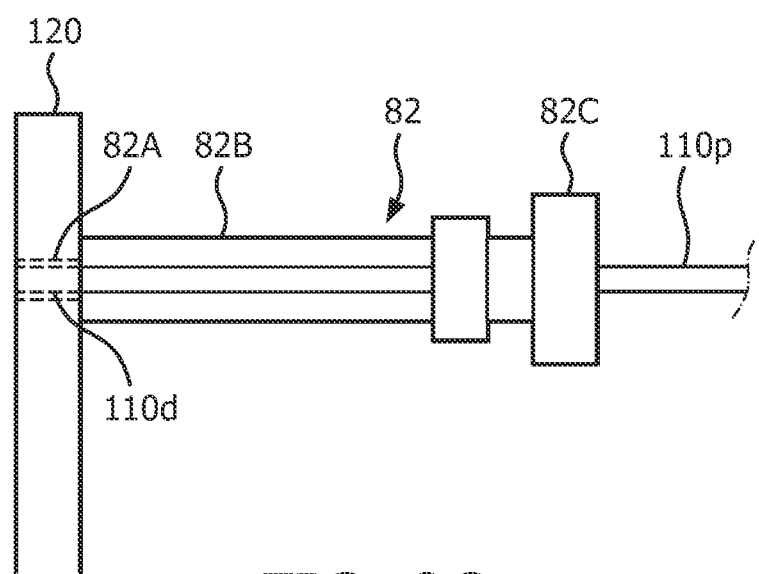

Referring to FIG. 9, an EM calibration tool 82 includes a cylindrical extrusion 82A extending from a primary cylindrical body 82B for holding an EM tracked tool, such as, for example, EM guidewire 110. As best shown in FIG. 9B, a distal end 110*d* of EM guidewire 110 is inserted through body 82B to the extrusion 82A, and a cap 82C is screwed upon body 82B to securely fix a distal end 110*d* of EM guidewire 110 within extrusion 82A. As best shown in FIG. 9C, extrusion 82A is dimensioned to snugly fit within a hole of a grid 120. As related to the adaptive mode of stage S104 (FIG. 8), EM calibration tool 82 may be inserted into specific holes of grid 120 utilized for needle/catheter insertion to thereby ensure highest accuracy for such grid holes.

Figure 11A:
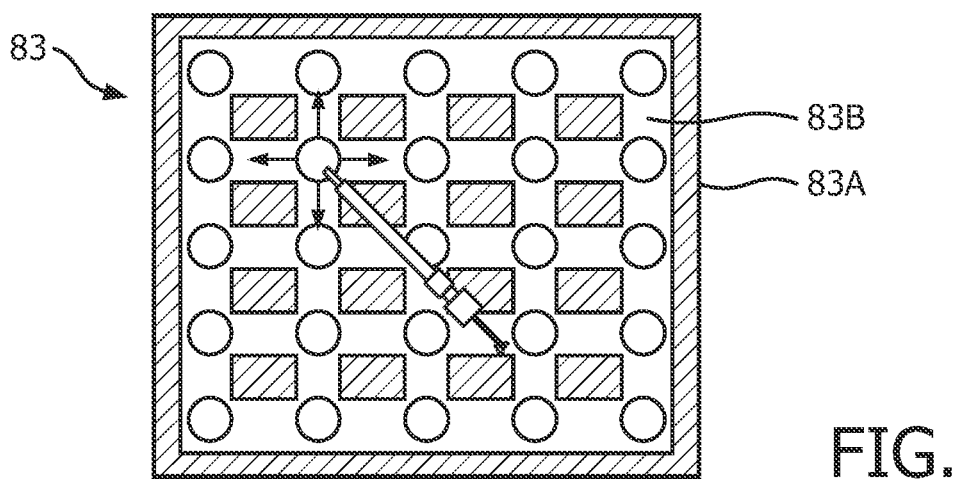
FIGS. 11A and 11B illustrate an exemplary embodiment of a grid calibration frame in accordance with the present invention.
Figure 11B:
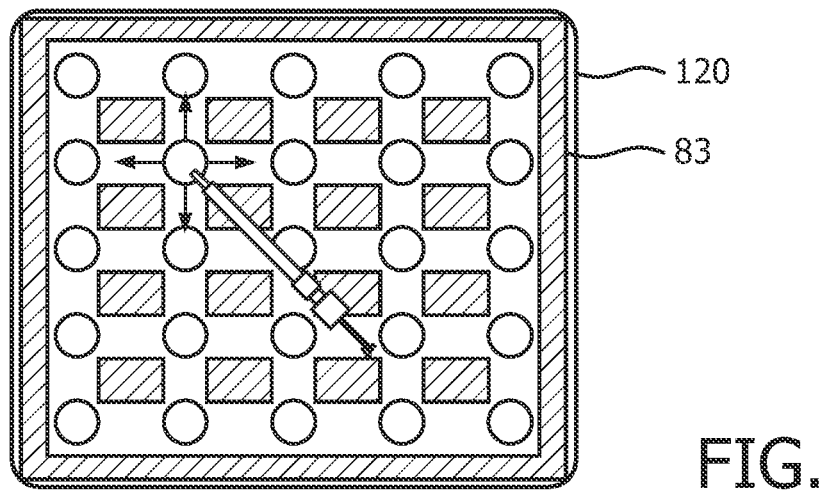

Referring to FIG. 11, grid calibration frame 83 includes a frame 83A having an array of continuous channels 83B sized to snugly fit extrusion 82A of EM calibration tool 82. As best shown in FIG. 11B, frame 83A is designed to be attached to a grid 120, and as tool 82 is manually or robotically traversed through channels 83B, EM calibration tool 82 may be inserted into one or more holes of a grid 120 to acquire EM data. In particular, as related to the adaptive mode of stage S104 (FIG. 8), EM calibration tool 82 may be inserted into specific holes of grid 120 utilized for needle/catheter/probe insertion to thereby ensure highest accuracy for such grid holes.

Alternatively, channel array 83A may omit the holes shown in FIG. 11A whereby intersections of channel array 83A are on top of the holes of grid 120 when the frame 83 is attached to grid 120. As such, EM calibration tool 82 is moved inside the channels without being inserted into any grid holes, and the EM-position of EM calibration tool 82 is recorded continuously to reconstruct the channel positions in the EM coordinate system. The recorded intersection points representative of the grid holes are localized in EM coordinate system using this data to calibrate the grid.

Figure 12:
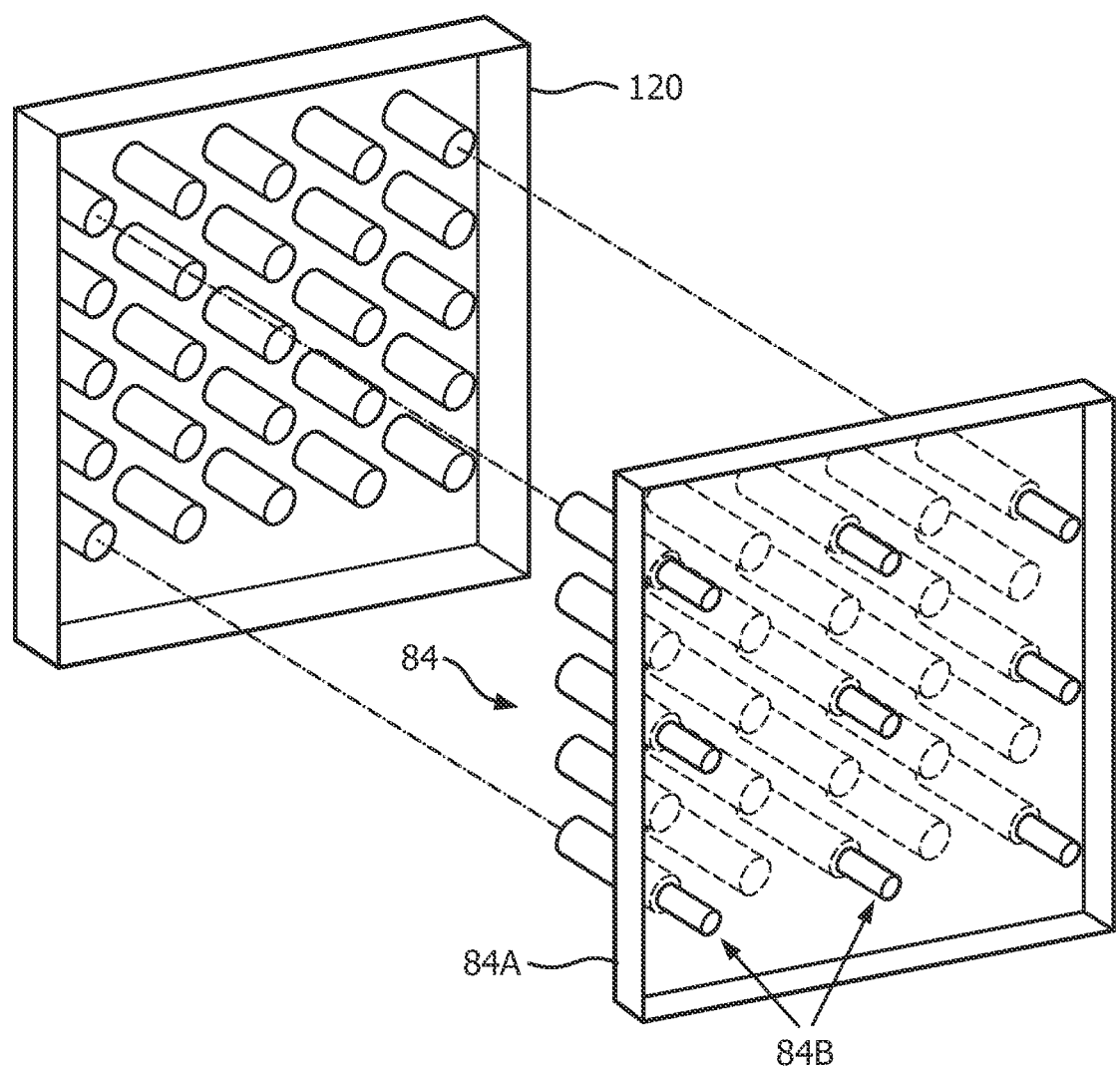
FIG. 12 illustrates an exemplary embodiment of a EM calibration frame in accordance with the present invention.

Referring to FIG. 12, EM calibration frame 84 has one or several EM position sensors 84B (e.g., five or six degrees of freedom DOF) attached to a frame 84A with a known calibration between the coordinate system of frame 84A and EM position sensors 84B. Frame 84A is briefly placed into grid 120, and the EM recording from EM positions sensors 84B is obtained, which allows direct calculation of the EM grid calibration without any manual positioning of a separate tracked tool. In one embodiment, EM position sensors 84B are sensor coils in known locations relative to frame 84A, and oriented perpendicular to the frame surface whereby the orientation of these sensor coils is identical to the orientation to a needle that may be pushed through holes of grid 120 during the clinical procedure. This identical alignment of the sensor coils ensures optimal EM tracking accuracy.

Referring back to FIG. 7, in practice, EM data acquirer 93 may automatically record EM data at each grid hole when utilizing EM calibration tool 82. Specifically, for manual control of EM calibration tool 82, EM data acquirer 93 evaluates an incoming EM data stream and detects when EM calibration tool 82 is stationary for a pre-determined period of time as an indication that EM calibration tool 82 has been positioned in the appropriate grid hole. A time threshold to detect whether user intends to save the current EM data as the desired coordinate corresponding to the grid hole may be set according to the preferences of the user. Alternatively, for robotic control of tool 82, EM data acquirer 93 may synchronize a recording of the data with an operation of the robot.

Also in practice, EM data acquirer 93 may notify the user of achieving a desired accuracy of calibration while reaching for more grid holes. The calibration fit error is calculated on the fly while more grid hole coordinates are recorded and once the desired pre-selected error is achieved, then the user is notified to stop reaching for more grid holes. The notification may be in the form of reporting an error value or showing a color representation (e.g., red for less accuracy than desired and green once reaching the desired accuracy). This is achieved by knowing the physical geometry of the grid and choosing grid holes in a specific order.

Referring to FIGS. 7 and 8, an accurate definition of a grid plane by EMDC workstation 91 is important to ensure that the data coordinate system used is in sync with the physical location of the grid and the prostate. This in turn ensures accuracy in needle/catheter/probe position estimation and 3D image reconstruction, and also allows further QA of the EM system.

Referring to FIG. 10, grid 120 was illustrated to facilitate an understanding of the EMDC system of the present invention. In practice, a grid/template may have any arrangement of holes/channels dependent upon a particular interventional procedure utilizing a EMDC system of the present invention.

Referring to FIGS. 1-9, those having ordinary skill in the art will appreciate numerous benefits of the present invention including, but not limited to, a quality assurance for validating and improving a performance accuracy of the EM tracking system and to an establishment of a patent coordinate system for EM tracking of interventional tools (e.g., ultrasound probes, catheters, needles, etc.).

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An electromagnetic tracking configuration system, comprising:
    an electromagnetic field generator operable to generate an electromagnetic field; and
    an electromagnetic data coordination system including a grid, the grid including at least one channel for guiding at least one interventional tool into an anatomical region, and
    at least one electromagnetic calibration tool, each electromagnetic calibration tool including at least one electromagnetic sensor, and configured to provide a known orientation and spatial relationship between at least one sensor and the grid; and an electromagnetic data coordination workstation operably connected to the at least one electromagnetic calibration tool, wherein, responsive to the electromagnetic field generator generating the electromagnetic field encircling a mechanical interaction of the at least one electromagnetic calibration tool with the grid, the electromagnetic data coordination workstation is operable to establish a coordination system for electromagnetically tracking an insertion of the at least one interventional tool through the grid into the anatomical region.

2. The electromagnetic tracking configuration system of claim 1, wherein the at least one electromagnetic calibration tool includes an electromagnetic calibration device configured and dimensioned to receive an electromagnetic guidewire;

wherein the electromagnetic calibration device has a distal extrusion operable to insert a distal end of the electromagnetic guidewire into the grid at a fixed depth; and wherein, responsive to the electromagnetic field generator generating the electromagnetic field encircling an insertion of the distal extrusion the electromagnetic calibration device into one of the channels of the grid, the electromagnetic data coordination workstation is further operable to acquire data indicative of an electromagnetic tracking of the channels of the grid.

3. The electromagnetic tracking configuration system of claim 1, wherein the at least one electromagnetic calibration tool includes a grid calibration frame operable to be attached to the grid;

wherein, upon being attached to the grid, the grid calibration frame includes a channel array extending across and intersecting at each channel of the grid, wherein the channel array comprises channels that extend in directions that are perpendicular to the axes of the channels of the grid;

wherein the at least one electromagnetic calibration tool further includes an electromagnetic calibration device configured and dimensioned to traverse the channel array of the grid calibration frame; and wherein, responsive to the electromagnetic field generator generating the electromagnetic field encircling the electromagnetic calibration device traversing the channel array of the grid calibration frame, the electromagnetic data coordination workstation is further operable to acquire data indicative of an electromagnetic tracking of the channels of the grid.

4. The electromagnetic tracking configuration system of claim 1, wherein the at least one electromagnetic calibration tool includes a grid calibration frame operable to be attached to the grid;

wherein, upon being attached to the grid, the grid calibration frame includes a channel array having a plurality of holes, one hole of the plurality of holes being aligned with each channel of the grid;

wherein the at least one electromagnetic calibration tool further includes an electromagnetic calibration device configured and dimensioned to traverse the channel array of the grid calibration frame and to be inserted with each hole of the grid calibration frame; and wherein, responsive to the electromagnetic field generator generating the electromagnetic field encircling the electromagnetic calibration device traversing the channel array of the grid calibration frame, the electromagnetic data coordination workstation is further operable to acquire data indicative of an electromagnetic tracking of the channels of the grid as the electromagnetic calibration device is inserted into each hole of the grid calibration frame.

5. The electromagnetic tracking configuration system of claim 1, wherein the at least one electromagnetic calibration tool includes an electromagnetic calibration frame operable to be attached to the grid;

wherein, upon being attached to the grid, the electromagnetic calibration frame includes an electromagnetic sensor inserted within one of the at least one channel of the grid;

wherein, responsive to the electromagnetic field generator generating the electromagnetic field encircling the at least one electromagnetic sensor inserted within the at least one channel of the grid, the electromagnetic data coordination workstation is further operable to acquire data indicative of an electromagnetic tracking of the channels of the grid.

6. The electromagnetic tracking configuration system of claim 1, further comprising:

an electromagnetic quality assurance system including
an electromagnetic sensor block including at least one electromagnetic sensor positioned and oriented to represent a simulated electromagnetic tracking of at least one interventional tool inserted through the electromagnetic sensor block into an anatomical region, and
an electromagnetic quality assurance workstation operably connected to the at least one electromagnetic sensor, wherein, responsive to the electromagnetic field generator generating the electromagnetic field encircling the at least one electromagnetic sensor, the electromagnetic quality assurance workstation is operable to test an electromagnetic tracking accuracy of the at least one interventional tool being inserted through the electromagnetic sensor block into the anatomical region.

7. The electromagnetic tracking configuration system of claim 6, wherein the electromagnetic sensor block includes at least one channel extending through the electromagnetic sensor block; and wherein each electromagnetic sensor is contained within one of the at least one channels.

8. The electromagnetic tracking configuration system of claim 6, wherein, responsive to the electromagnetic field generator generating the electromagnetic field encircling the at least one electromagnetic sensor, the electromagnetic quality assurance workstation is further operable to compute at least one metric indicative of a quality of electromagnetic tracking accuracy of a tracking location of each of the at least one electromagnetic sensor.

9. The electromagnetic tracking configuration system of claim 6, further comprising:

a reference electromagnetic sensor operable to be registered to the electromagnetic sensor block, wherein, responsive to the electromagnetic field generator generating the electromagnetic field encircling the at least one electromagnetic sensor and the reference electromagnetic sensor, the electromagnetic quality assurance workstation is further operable to compute at least one metric indicative of a quality of electromagnetic tracking accuracy of a tracking location of each of the at least one electromagnetic sensor.

10. The electromagnetic tracking configuration system of claim 9,
wherein, responsive to the at least one metric indicating a distortion within the electromagnetic field, the electromagnetic quality assurance workstation is further operable to correct the distortion within the electromagnetic field as a function of the electromagnetic tracking of the tracking location of each of the at least one electromagnetic sensor relative to a registered location of the reference electromagnetic sensor.

11. The electromagnetic data coordination system of claim 6,
wherein the at least one electromagnetic calibration tool includes an electromagnetic calibration device configured and dimensioned to receive an electromagnetic guidewire;
wherein the electromagnetic calibration device has a distal extrusion operable to insert a distal end of the electromagnetic guidewire into the grid at a fixed depth; and
wherein, responsive to the electromagnetic field generator generating the electromagnetic field encircling an insertion of the distal extrusion the electromagnetic calibration device into one of the channels of the grid, the electromagnetic data coordination workstation is further operable to acquire data indicative of an electromagnetic tracking of the channels of the grid.

12. The electromagnetic tracking configuration system of claim 6,
wherein the at least one electromagnetic calibration tool includes a grid calibration frame operable to be attached to the grid;
wherein, upon being attached to the grid, the grid calibration frame includes a channel array extending across and intersecting at each channel of the grid, wherein the channel array comprises channels that extend in directions that are perpendicular to the axes of the channels of the grid;
wherein the at least one electromagnetic calibration tool further includes an electromagnetic calibration device configured and dimensioned to traverse the channel array of the grid calibration frame; and
wherein, responsive to the electromagnetic field generator generating the electromagnetic field encircling the electromagnetic calibration device traversing the channel array of the grid calibration frame, the electromagnetic data coordination workstation is further operable to define a grid plane and acquire data indicative of an electromagnetic tracking of the channels of the grid.

13. The electromagnetic tracking configuration system of claim 6,
wherein the at least one electromagnetic calibration tool includes a grid calibration frame operable to be attached to the grid;
wherein, upon being attached to the grid, the grid calibration frame includes a channel array having a hole aligned with each channel of the grid;
wherein the at least one electromagnetic calibration tool further includes an electromagnetic calibration device configured and dimensioned to traverse the channel array of the grid calibration frame and to be inserted with each hole of the grid calibration frame; and
wherein, responsive to the electromagnetic field generator generating the electromagnetic field encircling the electromagnetic calibration device traversing the channel array of the grid calibration frame, the electromagnetic data coordination workstation is further operable to establish acquire data indicative of an electromagnetic tracking of the channels of the grid as the electromagnetic calibration device is inserted into each hole of the grid calibration frame.

14. The electromagnetic tracking configuration system of claim 6,
wherein the at least one electromagnetic calibration tool includes an electromagnetic calibration frame operable to be attached to the grid;
wherein, upon being attached to the grid, the electromagnetic calibration frame includes an electromagnetic sensor inserted within one of the at least one channel of the grid;
wherein, responsive to the electromagnetic field generator generating the electromagnetic field encircling the at least one electromagnetic sensor inserted within the at least one channel of the grid, the electromagnetic data coordination workstation is further operable to acquire data indicative of an electromagnetic tracking of the channels of the grid.

15. The electromagnetic tracking configuration system of claim 6, wherein the electromagnetic quality assurance workstation and the electromagnetic data coordination workstation are realized in a common hardware platform.

* * * * *